United States Patent [19]
Warden et al.

[11] Patent Number: 5,718,234
[45] Date of Patent: Feb. 17, 1998

[54] PHYSIOLOGICAL DATA COMMUNICATION SYSTEM

[75] Inventors: Stephen Nevin Warden, Cincinnati; Daniel M. Alley, Wyomming, both of Ohio

[73] Assignee: Northrop Grumman Corporation, Los Angeles, Calif.

[21] Appl. No.: 724,258

[22] Filed: Sep. 30, 1996

[51] Int. Cl.$^6$ .......................................................... A61B 5/04
[52] U.S. Cl. ............................................. 128/696; 128/903
[58] Field of Search .................................... 128/903, 904, 128/696; 370/95.1; 375/1

[56] References Cited

U.S. PATENT DOCUMENTS

| | | | |
|---|---|---|---|
| 5,142,534 | 8/1992 | Simpson et al. | 370/95.1 |
| 5,179,569 | 1/1993 | Sawyer | 375/1 |
| 5,381,443 | 1/1995 | Borth et al. | 375/1 |
| 5,381,798 | 1/1995 | Burrows . | |

*Primary Examiner*—Scott Getzow
*Attorney, Agent, or Firm*—Walter G. Stucliff

[57] ABSTRACT

The present invention provides for a communication system for conveying biomedical data between a plurality of patient monitors and a centralized base station. The communication system includes a plurality of base transceivers within the base station. Each of the base transceivers is coupled with a dedicated transmit antenna and a dedicated receive antenna. The communication system additionally includes a plurality of remote transceivers each coupled with one of the patient monitors. Each of the remote transceivers communicates with a respective base transceiver. Each of the base transceivers may be interconnected via a common bus. The base transceivers and remote transceivers each have at least one tuning device controlled by a microcontroller for varying the center frequency thereof according to a hop sequence. The communication system may include a forward error correction device, a scrambler and a modem for providing GMSK modulation of the biomedical data.

20 Claims, 11 Drawing Sheets

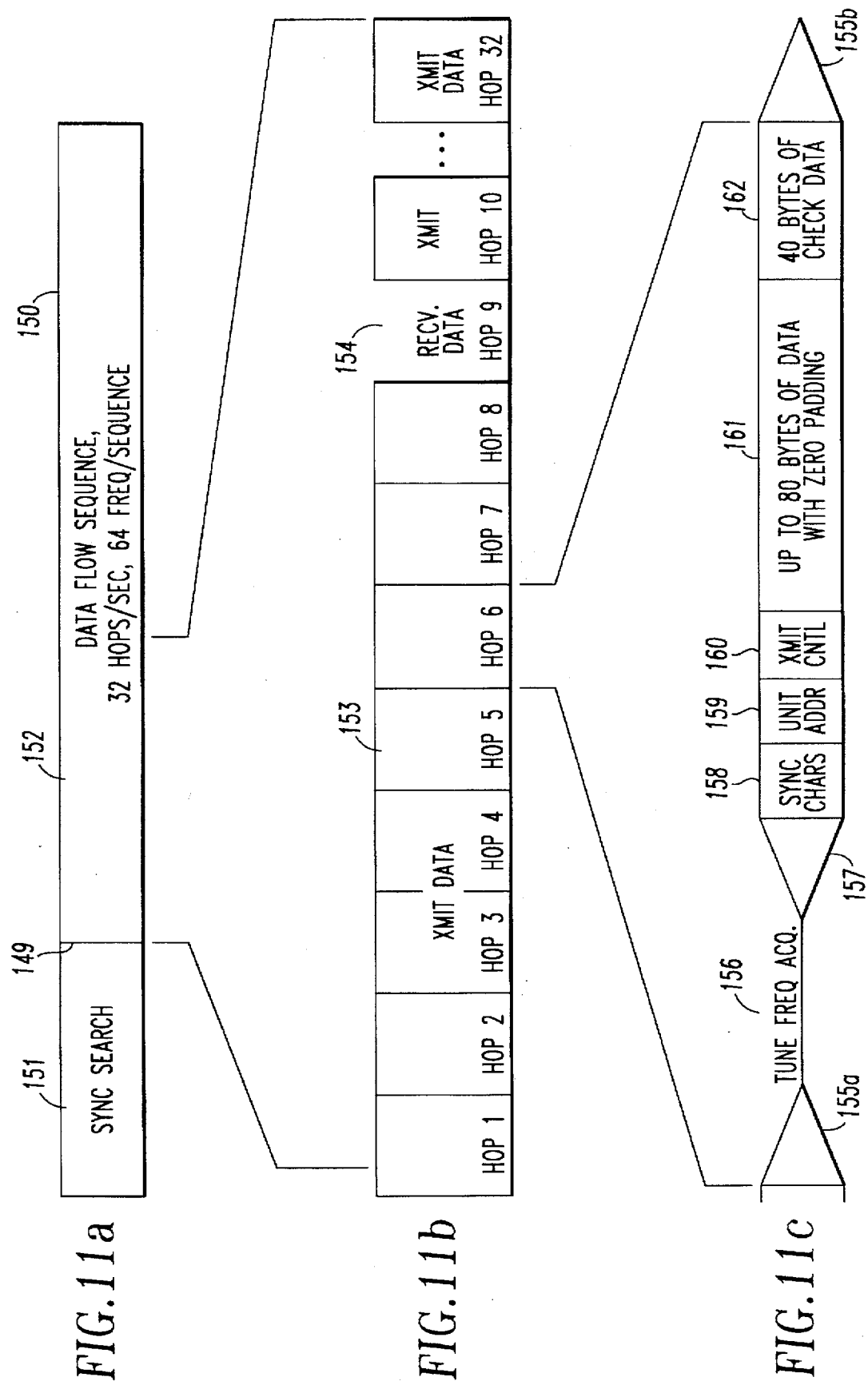

PHYSIOLOGICAL DATA COMMUNICATION SYSTEM

BACKGROUND OF THE INVENTION

1. Field of the Invention

The present invention relates to a communication system, and more particularly to a communication system for conveying biomedical data between a plurality of patient monitors and a base station.

2. Description of the Related Art

Biomedical data has been transmitted via telemetry systems which utilize FM analog modulation. The biomedical data obtained through a monitoring device attached to the patient was traditionally applied to a FM transmitter. A corresponding receiver tuned to an appropriate frequency of the transmitter was located at a centralized nurse's station to receive the biomedical data conveyed from the transmitter. The patient monitor and transmitter could be attached to the patient to permitting the patient to ambulate while being monitored.

However, the number of patients which may be simultaneously monitored at the centralized station is limited by the relatively large bandwidths associated with the analog modulation. Furthermore, the conventional communication devices would often trigger false alarms inasmuch as the analog biomedical data being communicated was susceptible to large amounts of DC drift.

Other conventional biomedical communication systems have used digital modulation to alleviate some of the aforementioned problems. These conventional devices have used frequency and phase shift keying modulation to improve the use of the carrier bandwidth compared with the traditional analog systems. While these devices provide more efficient use of the carrier bandwidth, they remain subject to DC drift.

More recent biomedical communication systems utilize direct sequence spread spectrum signaling methods to increase the number patients which may be monitored at a single centralized nurse workstation. In addition, the use of direct sequence spread spectrum technology in a communication system reduces the susceptibility of the biomedical signal to interference and noise.

However, these systems which utilize direct sequence spread spectrum transmission techniques have the drawbacks of high power consumption, wide RF bandwidth, and intolerance to multipath signals. The high power consumption is due to the high data rates within the modulator/demodulator (e.g., 1 to 10 Mb/s) leading to short battery life for the remote units. The wide RF bandwidth provides immunity to jamming by other wide bandwidth signals, however, a narrow bandwidth high power signal will cause the receiver to be jammed. Multipath will cause copies of the signal to be received with varying time shifts, causing the sequence synchronization to be lost with the data being jammed.

Frequency hopping spread spectrum is a low bandwidth form of transmission. Any jamming due to another narrow bandwidth transmitter is temporary, as the frequency hopping device will bounce to another frequency. Interleaving and error correction can be used to correct for any missed hops due to jamming. Adjacent frequency jamming is minimized by use of narrow bandwidth circuitry, whereas the direct sequence circuitry would be affected due to the higher bandwidth. Battery life is longer for frequency hopping devices, since the low data rates (e.g., 37.5 Kbps) result in lower digital logic clock rates and associated current draw.

SUMMARY OF THE INVENTION

The present invention provides for a communication system for conveying biomedical data between a plurality of patient monitors and a centralized base station. The communication system in accordance with the present invention includes a plurality of base transceivers within the base station. The communication system additionally includes a plurality of remote transceivers each coupled with one of the patient monitors.

Each of the base transceivers is coupled with a dedicated transmit antenna and a dedicated receive antenna. Each of the remote transceivers communicates with a respective base transceiver. Preferably, the remote transceiver transmits biomedical data obtained by the patient monitor to the base transceiver and may additionally receive data therefrom. Each of the base transceivers may be interconnected via a common bus.

The base transceivers and remote transceivers each have at least one tuning device, such as a phase lock loop, for varying the center frequency thereof. In addition, a microcontroller is coupled with the tuning devices for controlling the varying of the center frequency according to a hop sequence.

The hop sequence of each of the remote transceivers preferably corresponds to the hop sequence of a respective base transceiver. Additionally, the hop sequence of each of said base transceivers may be orthogonal to the hop sequences of the other base transceivers.

The remote and base transceivers of the communication system in accordance with the present invention may include a forward error correction device for reducing errors within the biomedical data communicated between corresponding transceivers. In addition, the remote and base transceivers may include a scrambler for scrambling and descrambling the biomedical data to remove bit redundancy therein and a modem for providing GMSK modulation and GMSK (Gaussian Minimum shift Keying) demodulation of the biomedical data.

A complete understanding of the invention will be obtained from the following description and the accompanying figures.

BRIEF DESCRIPTION OF THE FIGURES

FIG. 11a is illustrative of the contents of a typical RF data packet.

FIG. 11b is illustrative of a portion of the data hop sequence.

FIG. 11c is illustrative of the data transmission within a single transmit hop of the data hop sequence.

DESCRIPTION OF THE PREFERRED EMBODIMENTS

Figure 1:
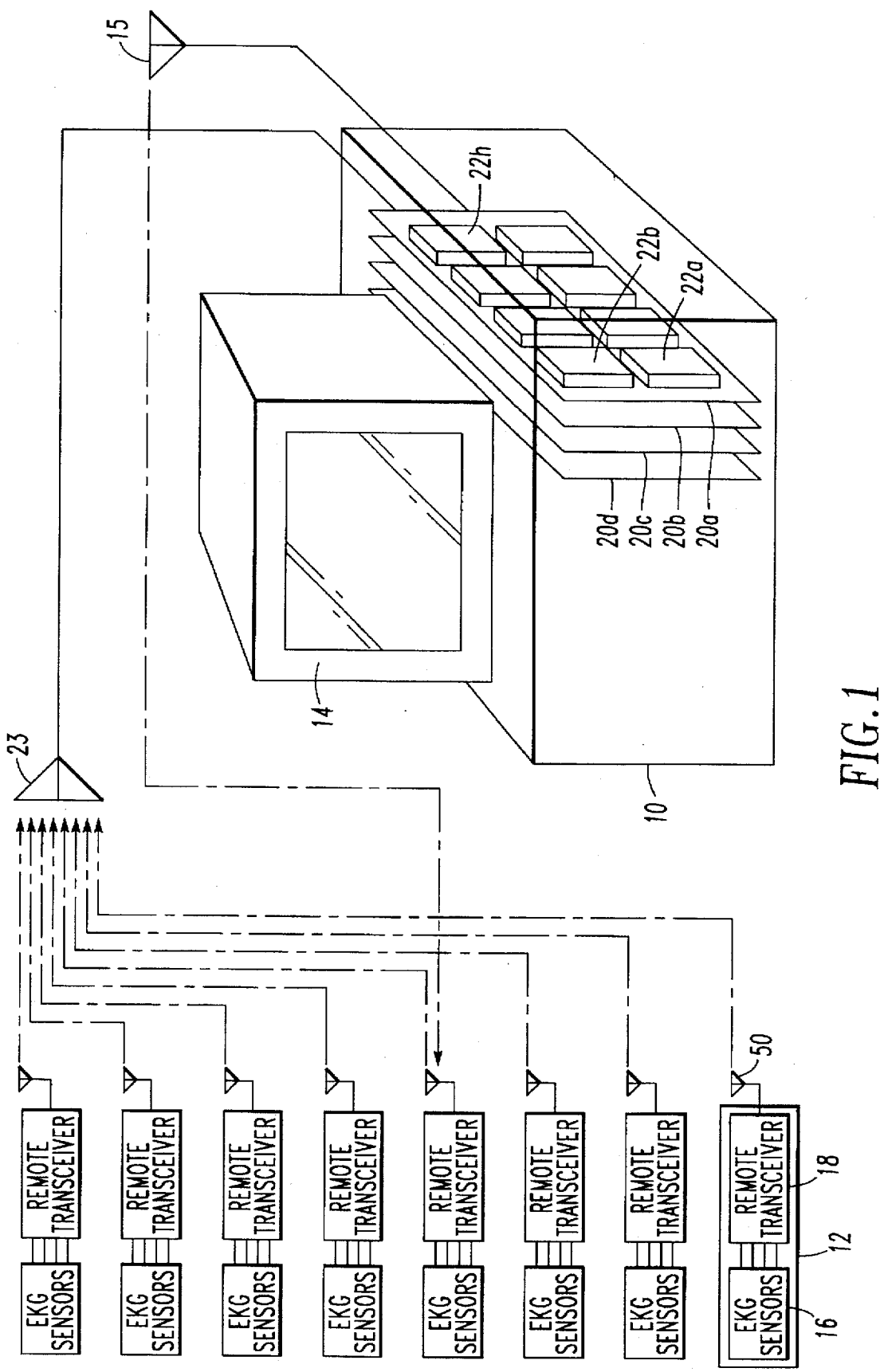
FIG. 1 is a graphical representation of the base station and a plurality of remote units of the communication system in accordance with the present invention.

Referring to FIG. 1, the invention provides a telemetry system including a base station 10 and a plurality of remote units 12 for transmitting data between a nurse or central monitoring station and a plurality of patients. The telemetry system may operate within the unlicensed 902 MHz to 928 MHz Industrial, Scientific, Medical (ISM) band.

As shown in FIG. 1, the telemetry system in accordance with the present invention includes a base station 10. The base station 10 communicates with the remote units 12 and may convey information from the remote units 12 to a user through an interface such as a display 14. The display 14 may convey EKG traces and other biomedical data (i.e., patient blood pressure, pulse, etc.) from the remote units 12 to an attendant nurse.

The remote units 12 include a patient monitor 16 coupled with a remote transceiver 18. The patient monitor 16, such as a Criticare Systems Inc., Model 2200 "Scholar Monitor", measures physiological data (e.g., EKG data) from the patient. The data is applied to the remote transceiver 18 which communicates with the base station 10. The base station 10 includes at least one base transceiver 22 which preferably individually communicates with a respective remote transceiver 18.

In practical applications, it is desirable to have numerous remote units 12 for providing continuous patient information of numerous patients to a single base station 10. Therefore, the base station 10 may include a plurality of base transceivers 22 and each base transceiver 22 may communicate with a respective one of the plurality of remote transceivers 18.

The base transceivers 22 may be arranged in base interfaces 20. Four base interfaces 20a–20d are shown in FIG. 1 and each base interface 20 may contain eight base transceivers 22 for communicating with eight remote units 12 and therefore permitting a single base station 10 to monitor data from 32 patients.

Software running on each base station 10 may provide a graphical representation via display 14 of the remote unit 12 biomedical data from each patient. A plurality of displays 14 may be required to simultaneously display the biomedical data from all patients.

The base interfaces 20 provide both RF interconnects to a dedicated receiver antenna 23 and a dedicated transmit antenna 15 of each base station 10. Transmit antenna 15 and receiver antenna 23 are intended to reduce cosite interference at the base station 10, where the signal(s) being transmitted by the base transceivers 22 do not cause interference to the other base transceivers 22 within the base station 10. With additional reference to FIG. 2, if a single antenna were used, the relatively higher power transmit signals reflected from the antennas due to less than perfect VSWR (Voltage Standing Wave Ratio) matching (never perfect in actual implementations) would be larger than the intended receive signal causing distortion in the overloaded input stage of receiver 112. Two antennas allow the receive antenna 23 to be far enough away from the transmit antenna 15 to reduce the coupled signal below the receiver distortion level.

As used herein, transmit antenna 15 and receive antenna 23 each may refer to a single dedicated antenna or a dedicated antenna array. Each base interface 20a–20d and each base transceiver 22a–22h therein is coupled with the transmit antenna 15 via a transmit port 42. Further, each base interface 20a–20d and each base transceiver 22a–22h therein is coupled with the receive antenna 23 via a receive port 41.

The base interfaces 20 additionally include digital interfaces for command and data flow from the base station 10 to each base transceiver 22 therein.

In some environments it may be desirable to provide numerous base stations 10 to increase the monitoring capability and capacity. Each base station 10 may therefore may include serial timing cable for intra-transceiver communications to allow coordination of timing. Such communications are necessary for frequency hop timing and transmitter interaction.

Figure 2:
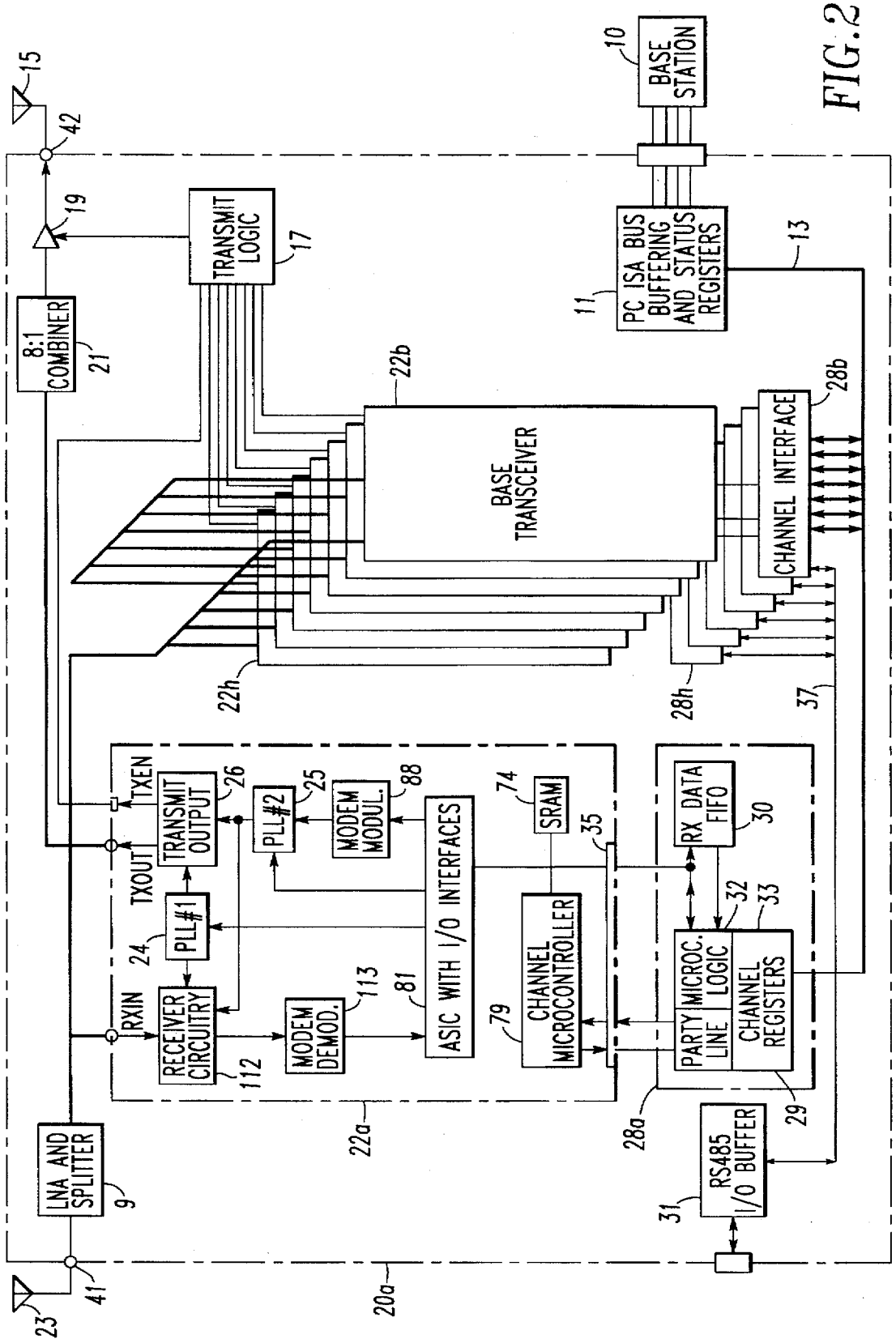
FIG. 2 is a block diagram of an embodiment of a base interface within the base station.

An embodiment of a base interface 20 within a base monitor 10 is shown in FIG. 2. The base interface 20 may include a plurality of base transceivers 22a–22h (first base transceiver 22a is shown in detail and is representative of the other base transceivers 22b–22h).

Biomedical information may be received at antenna 23 and forwarded to a low noise preamplifier\splitter 9 for filtering and amplification. The preamplifier\splitter 9 is coupled with each base transceiver 22. Each base transceiver 22 may include a receiver 112, first phase lock loop (PLL) 24, second phase lock loop 25, transmit output 26, modem modulator 88, modem demodulator 113, ASIC (Application Specific Integrated Circuit) 81, microcontroller 79, and SRAM 74 (Static Random Access Memory).

The transmit output stage 26 may forward a transmit enable signal to transmit enable logic 17 for triggering output amplifier 19. Any base transceiver 22 may control the amplifier 19 via logic 17. Data being transmitted to a remote transceiver 18 from the base transceiver 22 passes from the transmit output 26 to a combiner 21 and is amplified in output amplifier 19 before transmission via transmit antenna 15.

Each base interface 22a–22h is coupled with a respective channel interface 28a–28h. The channel interfaces 28a–28h include a channel FPGA (Field Programmable Gate Array) 29 and FIFO memory device 30. The FIFO (First In First Out) memory device 30 temporarily stores data from a remote transceiver 18 received by the microcontroller 79 within a respective base transceiver 22 until it is accessed by the base station 10. The channel FPGA 29 includes a party line section 31, microcontroller logic 32 and channel registers 33.

The serial party line section 31 is coupled with a bidirectional party line 37 for timing and communications between base transceivers 22 on a single base interface 20a as well as other base interfaces 20b–20d via a RS485 I\O buffer 34.

Figure 3:
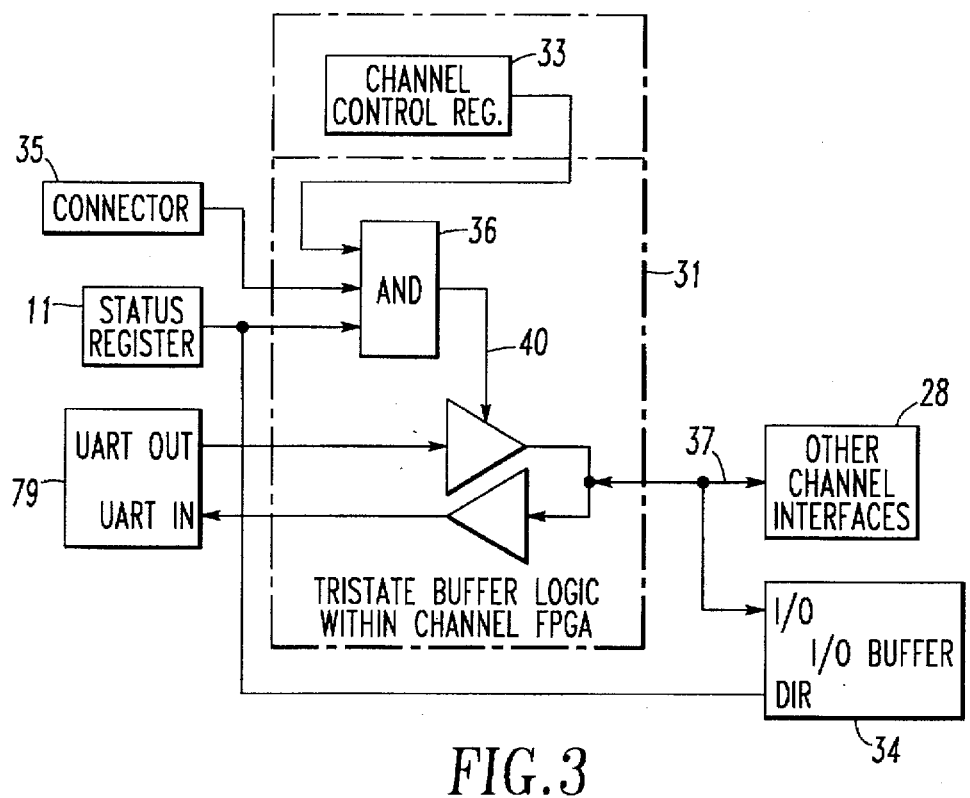
FIG. 3 is a logic diagram of a serial timing interface within the FPGA of each base transceiver.

The serial party line section 31 coordinates transmissions from the respective base transceivers 22. The microcontroller 79 within each base transceiver 22 senses the party line 37. An embodiment of a serial timing interface 38 within the channel FPGA 29 is shown in detail in FIG. 3.

A respective microcontroller 79 will write to a channel register 33 once it decides to drive the party line 37. The channel register 33 is coupled into AND gate 36. A CHANNEL THERE signal is also applied to the AND gate 36 from the respective base transceiver 22 through the connector 35. This signal indicates that the particular base transceiver 22 has been installed. If the base station 10 is installed with a reduced number of base transceivers 22, then the base interface 20 could have connectors 35 that do not attach to the base transceivers 22. In this event, CHANNEL_THERE is not connected and will default to a known logic state to allow the channel interface FPGA 29 to be disabled so as not to drive the party line 37 or internal data bus 13 due to floating inputs to the FPGA 29 internal logic. This signal indicates that the particular base transceiver 22 has been installed.

A final control signal, Time_Master, from the ISA bus status registers 11 is applied to the AND gate 36 to serve as a timing enable function from the base station 10 and is used to control the direction of the signal flow in the RS485 I/O buffer 34. This combination of signals controls the particular timing when each respective microcontroller 79 may drive the party line 37.

The microcontroller 79 may output a signal via UART (Universal Asynchronous Receiver Transmitter) OUT to the party line 37 once the three signals are present at the AND gate 36. The signal is forwarded to I\O buffer 34 and the remaining channel interfaces 28. Input from the party line 37 may be applied to the microcontroller 79 via UART IN when the microcontroller 79 is not transmitting.

Whenever the base station 10 software selects a base transceiver 22 to be a timing reference for all other base transceivers 22 in that base group, it will send a sequence of commands via the ISA interface 11. The selected transceiver's microcontroller 79 will sense the command being loaded in the channel FPGA 29 channel register 33. Upon interpreting the command, the channel FPGA 29 microcontroller logic 32 will be controlled to assert the ENABLE_PARTY_LINE signal 40. The base station 10 will then write to the ISA interface status register 11 to assert the TIME_MASTER signal. This causes the AND gate 36 to enable the output driver such that any signal at the microcontroller 79 UART_OUT will pass to the serial party line 37 and be sensed by all other microcontrollers 79 that monitor the party line 37. TIME_MASTER also is used to enable the direction of flow through the RS485 buffer 34, with the buffer 34 being an output driver when TIME_MASTER is asserted. When the base interface 20 containing transceivers 22 is not selected by the base station 10 as a timing reference, TIME_MASTER is de-asserted and the serial data flows into the party line 37 from the RS485 buffer 34. This allows transceivers 22 on other interfaces 20 to monitor timing using a wired connection between the buffers 34.

A local data and control bus 13 interconnects each base transceiver 22 on a base interface 20. In addition, bus 13 connects the base interfaces 20 through the buffer 11 to the base station 10. The base station 10 controls the flow of information from the base transceivers 22 to the base station 10 via buffer 11.

Figure 4:
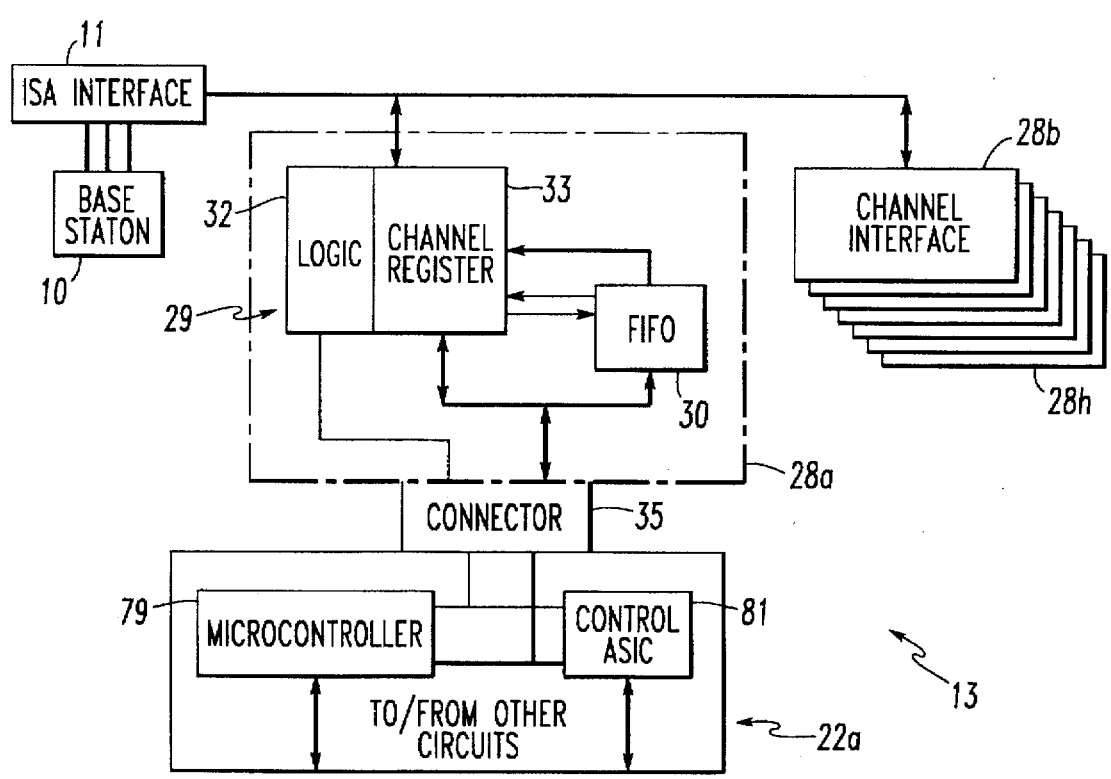
FIG. 4 is a functional block diagram of the base transceiver interface to the bus within the base interface.

The ISA bus 13 interconnecting a base transceiver 22 and the base station 10 is shown in detail in FIG. 4. The bus 13 is coupled with a channel FPGA 29 containing microcontroller logic 32 and channel registers 33. The channel registers 33 include a decode FPGA for control of the local bus 13 and IRQ (Interrupt Request) sensing and the channel registers 33 are interfaced to the base transceiver connectors 35.

The base station 10 may operate with registers within the ISA interface 11 to monitor: whether the base transceiver 22 is plugged in and transmitting or receiving (read only); the presence of an interrupt from the base transceiver 22 (read only); the Time_Master signal from the base station 10 (read\write).

Figure 5:
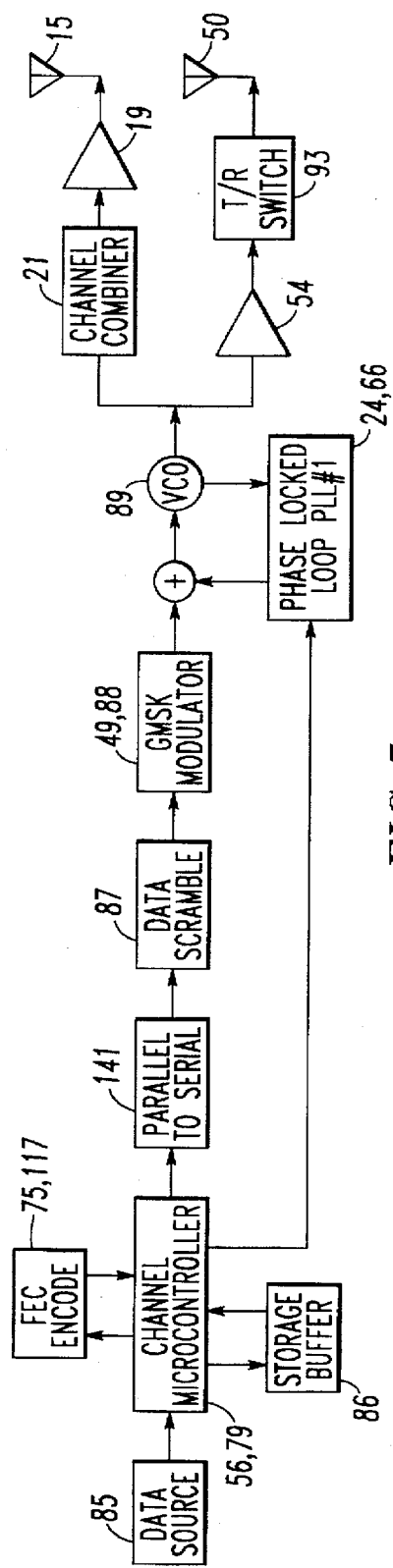
FIG. 5 is a functional block diagram of the data flow of a transmit signal with the remote transceiver and base transceiver.

FIG. 5 shows the data flow for a transmit signal within the remote transceiver 18 and base transceiver 22. The transmit data originates within the data source 85. The data source 85 may be bursts of parallel data loaded by the base station 10 using a command\response sequence through a channel FPGA 29 attached to a base transceiver 22. Alternatively, the data source 85 may be bursts of serial data at 19.2 Kbaud through the RS232 interface 72 from the patient monitor 16 within the remote unit 12 (FIG. 7).

FIG. 5 shows both paths of data flow for transmit signals from both the remote transceiver 18 and the base transceiver 22. The channel combiner 21 is not required in the remote transceivers 18 and the transmit\receive switch 93 is not required in the base transceivers 22.

Figure 7A:
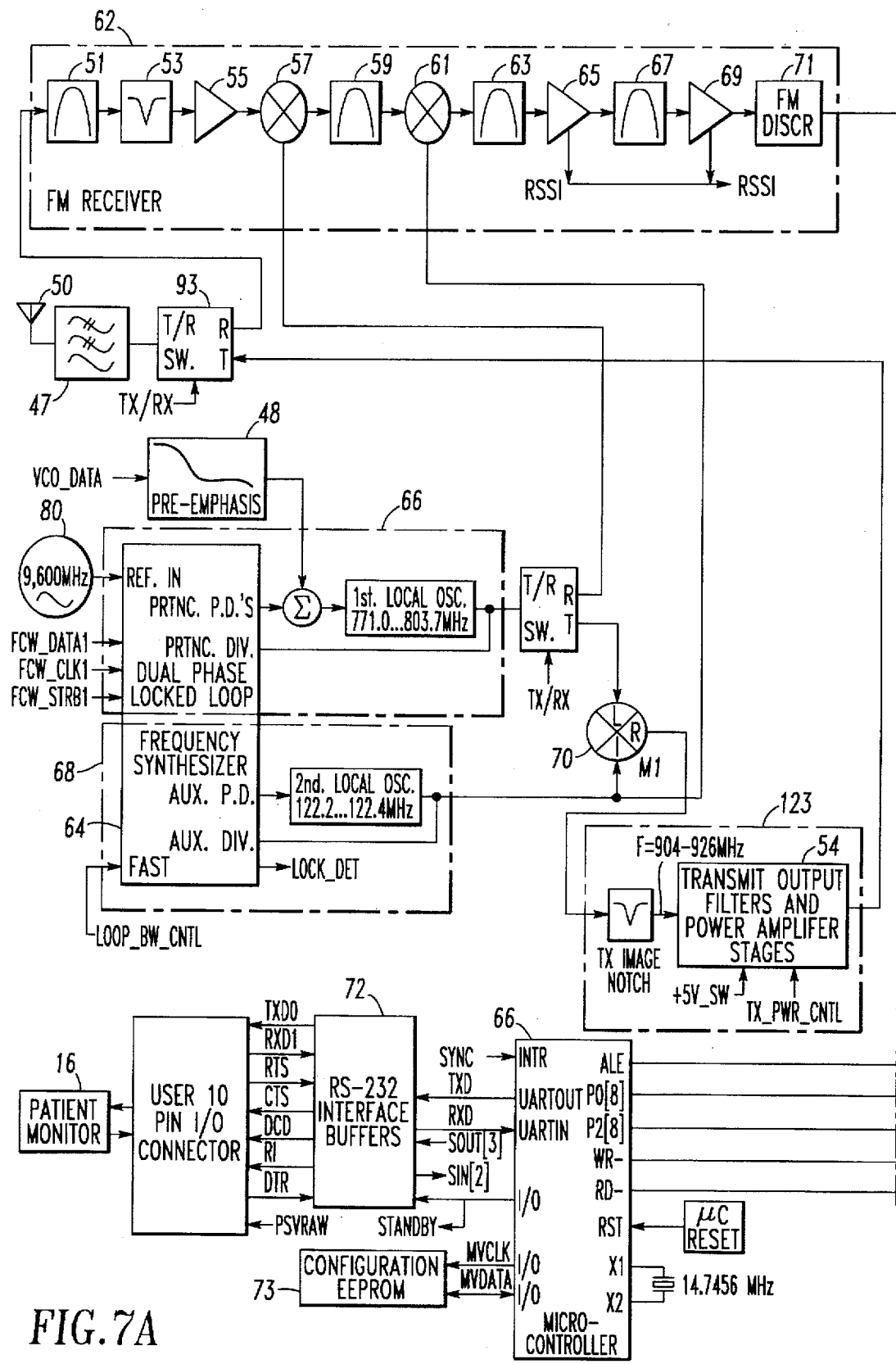
FIG. 7 is a schematic diagram of an embodiment of the remote transceiver.
Figure 7B:
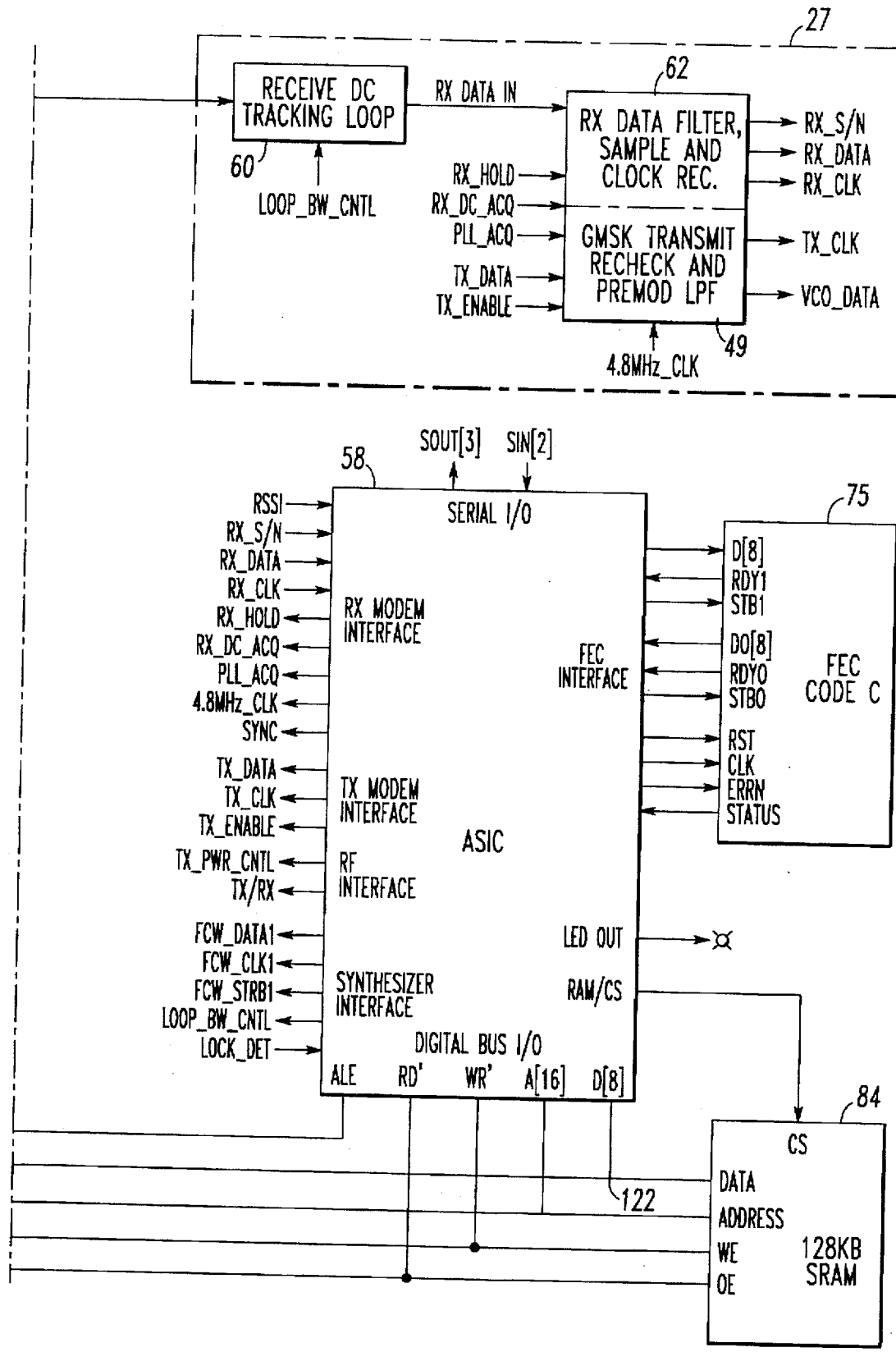

With additional reference to FIG. 2 and FIG. 7, a respective microcontroller 56,79 queues the data within a storage buffer 86 present in a respective SRAM 74,84. The microcontroller 56,79 may then perform FEC (Foward Error Correction) operations through a respective FEC device 75,117. The FEC device 75,117 may generate 40 bytes of check data for every 80 bytes of data. In particular, Reed-Solomon codes may be utilized for the FEC encoding. The codes are discussed in "Primer: Reed-Solomon Error Correction Codes (ECC)" and "Interleaving For Burst Error Correction," both articles are published by Advanced Hardware Architectures, Inc. in Pullman, Wash., and both articles are incorporated herein by reference.

The microcontroller 56,79 generates RF transmit packets from the FEC device 75,117 output and address information. Each RF transmit packet is sent by the microcontroller 56,79 as writes to a transmit shift register 141 within the ASIC 58 at a rate of 213 μsec\byte.

The output of the shift register 141 is applied to scrambler 87 within a respective ASIC 58,81 to avoid long strings of identical data in order to maintain proper recovery at the respective receiver 52,112. The output of the scrambler 87 is clocked into the GMSK modulator 49,88 at a rate of 37500 bits\sec. The GMSK modulator 49,88 forms an analog modulation signal from the scrambled data signal.

The choice of modulation type (e.g., GMSK vs. PSK (Phase Shift Keying) or any other scheme) is based on the application: low power, moderate data rate, and multiple devices using the same spectrum (e.g., up to 7 groups of 32 users). The Gaussian Minimum Shift Keying is a modulation type that attempts to minimize the side lobes on the output spectrum which in turn allows for tightly packed adjacent signals (e.g., 37.5 Kbps within a 50 KHz spectrum channel). The modem 27, 120 is also available in a low power integrated circuit using few additional components. If other modulation were used, either the power drain would be increased or there may be fewer possible users due to fewer hop frequencies within the band.

The analog modulation signal is summed with the PLL control voltage 89 to FM modulate the transmit RF signal. The microcontroller 56,79 may control the tuning parameters of the PLL synthesizer 64, 82.

The channel RF signal may be combined before transmission with other channels in combiner 21 (only present in the base transceiver 22) which is coupled with RF output connector 77. The transmit signal is subsequently applied to power amplifier 19 and sent to the transmit antenna 15.

The transmit signal may be applied to the transmit\receive switch 93 (only present in a remote transceiver 18). The transmit\receive switch 93 may be implemented within the remote transceivers 18 for permitting both transmit and receive data to be sent via a single antenna 50. The transmit\receive switch 93 may be switched via ASIC 58 to control data flow.

Figure 6:
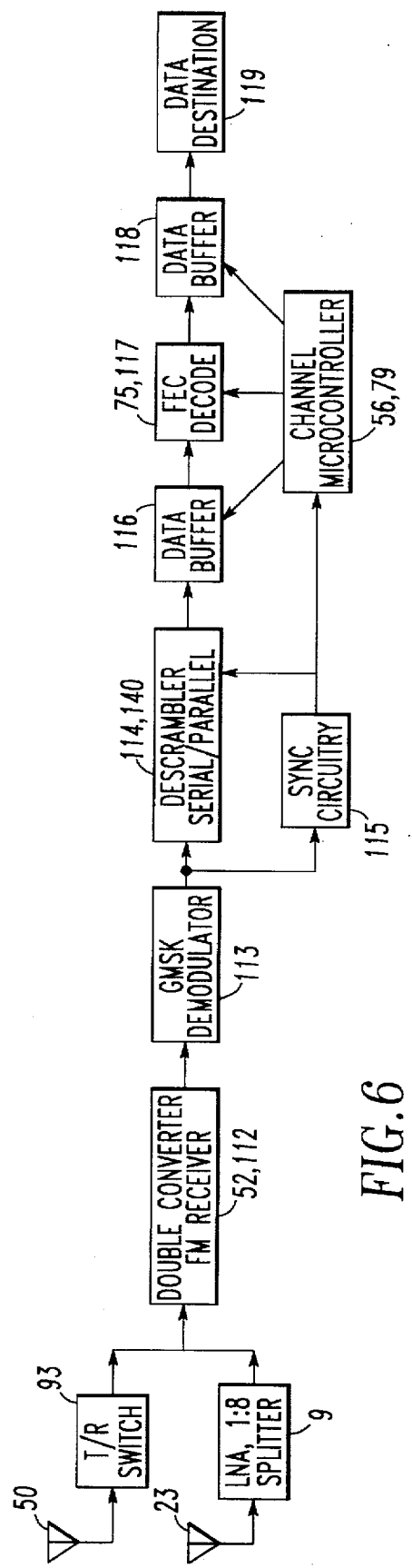
FIG. 6 is a functional block diagram of the data flow of a receive signal with the remote transceiver and base transceiver.

The data flow for the receive signal is shown in FIG. 6 for both the remote transceiver 18 and base transceiver 22. In particular, the FM signal (904–928 MHz) is received at base station 10 by a receive antenna 23 and may be applied to a LNA 1:8 splitter 9 within the base interface 20. Alternatively, the FM signal may be received at a remote transceiver 18 by an antenna 50. The FM signal may thereafter be applied to a transmit/receive switch 93 permitting the use of a single antenna 50 for both transmit and receive.

The signal is subsequently down converted in the receiver 52,112 from the FM signal to the baseband signal. The baseband signal is applied to the respective GMSK demodulator 62,113 within the modem 27,120. The GMSK demodulator 62,113 tracks and phase locks on the embedded data clock and reclocks out the received data signal.

The demodulated signal is next applied to synchronization circuitry 115 and a descrambler 114 both within a respective ASIC 58,81. The synchronization circuitry 115 allows for bit and byte alignment of the serial data. The descrambler 114 reverses the transmitter's scrambler operations and generates parallel data within a serial parallel shift register 140.

The parallel data is buffered by the microcontroller 56,79 in data buffer 116 within respective SRAM 74,84. The microcontroller 56,79 reads the parallel data from the ASIC 58,81 using interrupt routines. The data is applied to the respective FEC device 75,117 wherein the decoding converts the 120 byte blocks to 80 byte blocks, thus removing the correction data. The output of the FEC device 75,117 is applied to a second data buffer 118 within the respective SRAM 74,84. The microcontroller 56,79 queues the data and passes the information to a data destination 119. The data destination 119 may be either a serial UART within the remote unit 12 or a data FIFO 30 within the base transceiver 22 for reading by the base station 10 via the data bus 13.

Each remote unit 12 includes a patient monitor 16 coupled with a remote transceiver 18. An embodiment of a remote transceiver 18 is shown in The remote transceiver 18 includes an antenna 50 coupled with a harmonic filter 47 having a center frequency of 1 GHz. The antenna 50 may be switched between the receiver 52 and the transmit output stage 54 through a transmit/receive switch 93. Switching between the receive and transmit modes of operation, as well as power control, is performed by a microcontroller 56 which utilizes control logic within the ASIC 58 to control switch 93. Preferably, the microcontroller 56 turns off the transmit circuitry during a receiving mode of operation to provide power savings.

The receiver 52 is preferably a conventional double conversion FM device which mixes the input frequency (e.g., 904 MHz–928 MHz) to provide a first intermediate signal at a first frequency (e.g., 133 MHz). A first bandpass filter 51, image notch filter 53, amplifier 55, first mixer 57, second bandpass filter 59 within the receiver 52 may be utilized to provide the first intermediate signal. First bandpass filter 51 may have a center frequency of 915 MHz and a bandwidth of 20 MHz, the notch filter 53 may have a center frequency of 650 MHz and a bandwidth of 50 MHz and the second bandpass filter 59 may have a center frequency of 133 MHz and a bandwidth of 2 MHz.

The first intermediate signal is subsequently remixed to form a second intermediate signal at a second frequency (e.g., 10.7 MHz). A second mixer 61, bandpass filters 63,67 and amplifiers 65,69 may be utilized to generate the second intermediate signal. The bandpass filters 63,67 may each have a center frequency of 10.7 MHz and a bandwidth of 85 KHz. The second intermediate signal drives a FM discriminator 71.

The output of the FM discriminator 71 is applied to a modem 27 and sensed by a tracking loop filter 60 to maintain an average DC component before being applied to a GMSK demodulator 62. The GMSK demodulator 62 extracts the data clock signal and reclocks the data information. The clock and data information are passed to the ASIC device 58 which synchronizes and packs the binary bit stream into parallel data before being applied to the microcontroller 56.

Tuning of the remote receiver 52 may be performed by a dual PLL synthesizer 64 with the tuning data written by the microcontroller 56 into ASIC registers followed by the ASIC 58 serially clocking the information to the synthesizer 64. The first and second phase lock loops 66,68 are shown in FIG. 7. The reference for the PLL synthesizer 64 is a 9.6 MHz oscillator 80 providing a discrete frequency spacing of 50 KHz.

The receiver 52 is preferably powered off when the remote transceiver 18 is transmitting. In addition, the two local oscillators are beat together at mixer 70 to form the transmit frequency and to allow proper frequency spacing. The first local oscillator 66 is FM modulated by a signal added to the voltage controlled oscillator of the PLL synthesizer 64. Digital data from the patient monitor 16 is written to the ASIC 58 by the microcontroller 56 via RS232 interface 72. The digital data encoded in FEC device 75 and the ASIC 58 serially shifts the data to the GMSK modulator 49 within modem 27. The output of the GMSK modulator 49 is applied to a pre-emphasis filter 48 prior to adjusting the VCO of the PLL synthesizer 64 in order to compensate for following stages' frequency responses in the transmitter and receiver circuitry.

The remote transceiver 18 is coupled with the patient monitor 16 via a RS232 duplex serial connection 72 with flow control using CTS (Clear To Send) and RTS (Request To Send) signals. The microcontroller 56 serves as a control device which manages the tuning of the remote transceiver 18, timing of the transmissions, power control, and buffering the serial data arriving both from the patient monitor 16 via the RS232 connection 72 and the receiver 52.

Configuration information is stored in an electrically erasable programmable memory (EEPROM) 73 and working data is saved in a SRAM device 84. Forward error correction operations are performed on the data by the microcontroller 56 via interfaces within the ASIC 58 to a FEC device 75. The FEC interfaces provide correct timing to the FEC encoder 75 and allow asynchronous operation by the microcontroller 56.

Figure 8A:
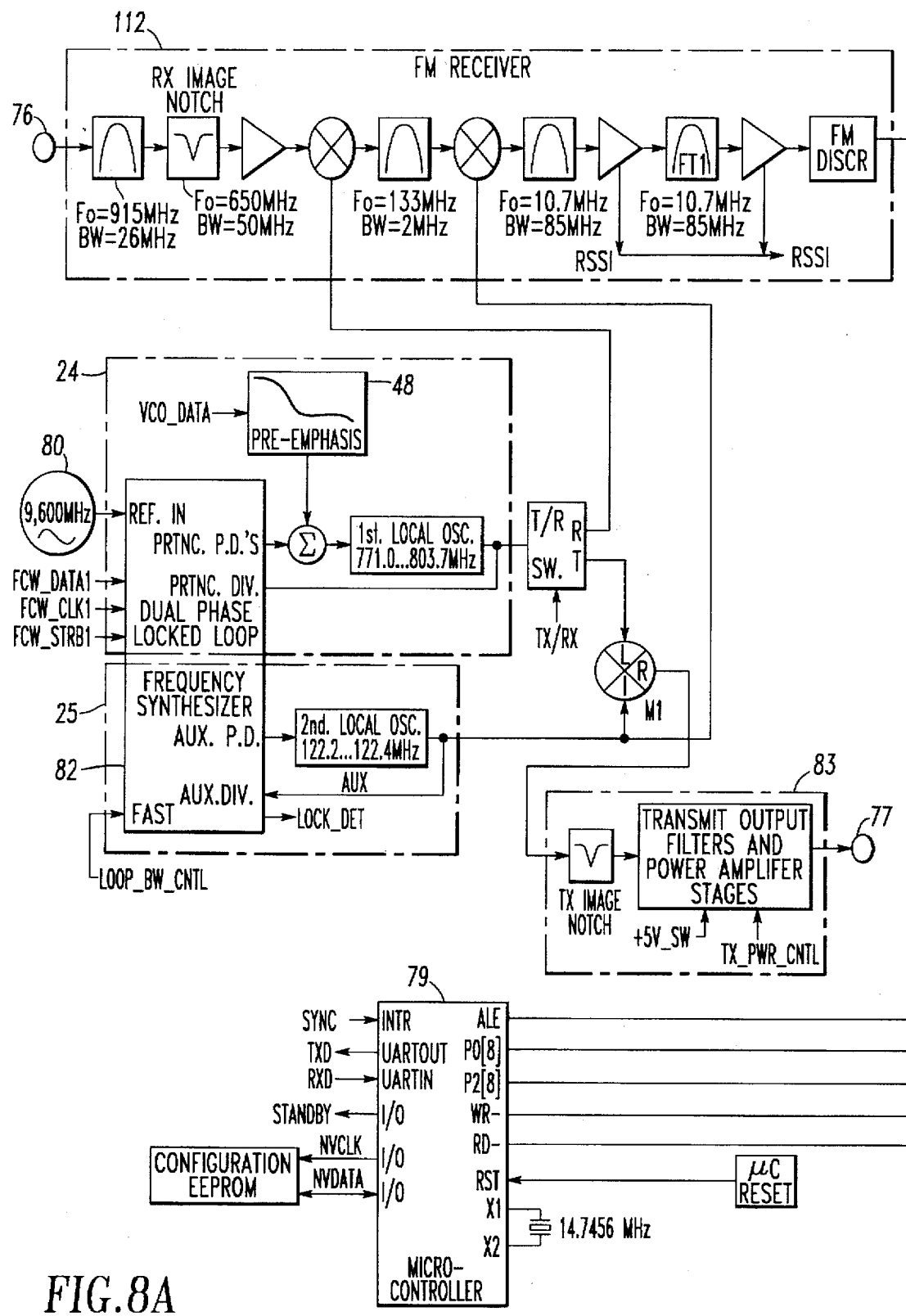
FIG. 8 is a schematic diagram of an embodiment of the base transceiver.
Figure 8B:
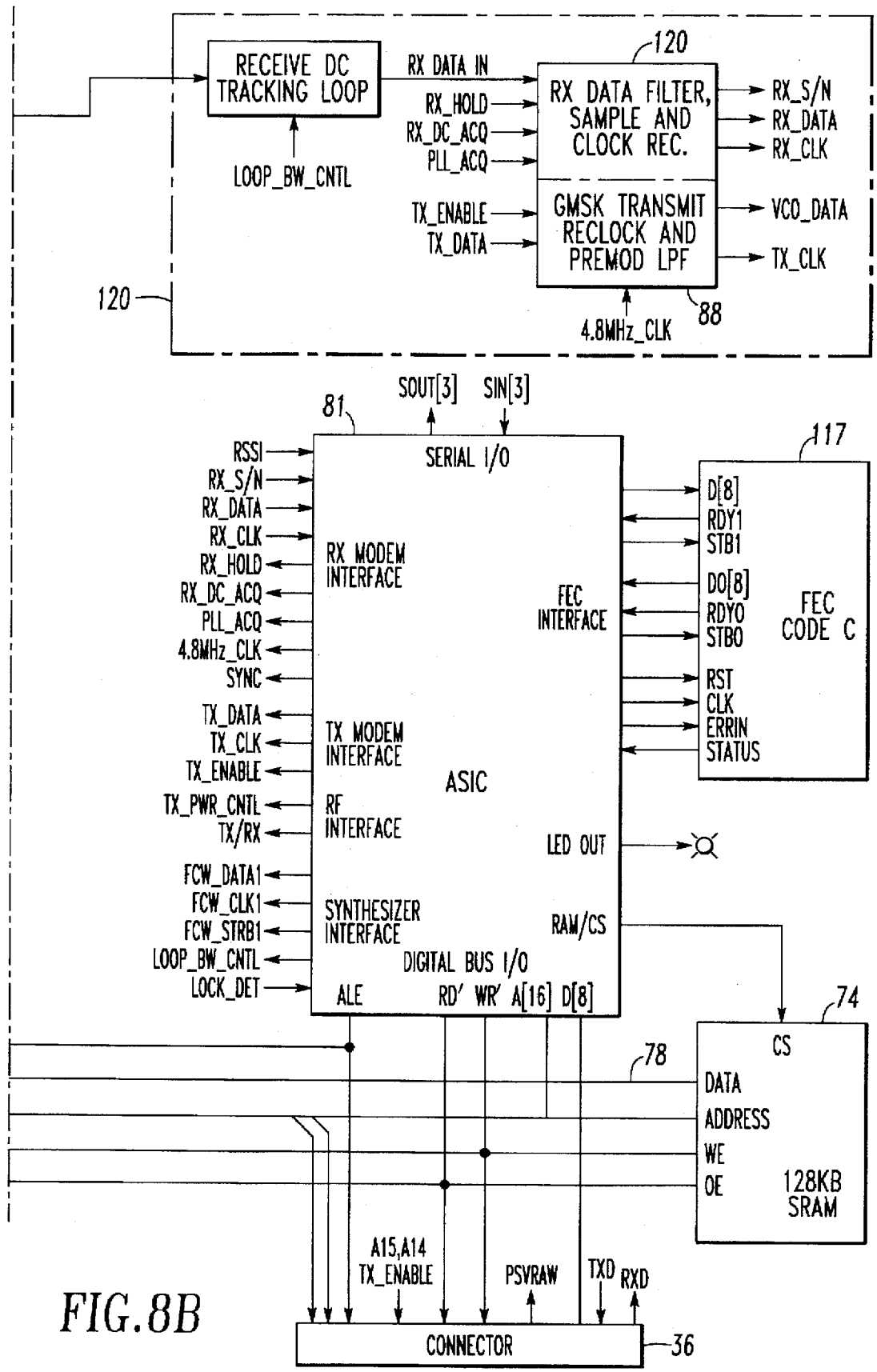

An embodiment of a base transceiver 22 is shown in FIG. 8. The base transceiver 22 may be similar to the remote transceiver 18. In particular, one difference between the base transceiver 22 and the remote transceiver 18 is at the RF connections. The base transceiver 22 has separate RX (receive) and TX (transmit) inputs as indicated by RF input connector 76 and RF output connector 77. The RF connectors are individually coupled with a dedicated receive antenna 23 and a dedicated transmit antenna 15 (antennas 15,23, splitter 9, combiner 21 are not shown in FIG. 8).

In addition, the base transceiver 22 includes a digital bus 78. The microcontroller 79 data bus, upper address lines, and several control signals are passed through a 40 pin connector 35 to channel interface 28. This allows the microcontroller 79 to have access to the FPGA 29 for coordinating parallel transfers to the base station 10 using registers 33 and an output FIFO 30 (for received data into the base transceiver 22).

Figure 9:
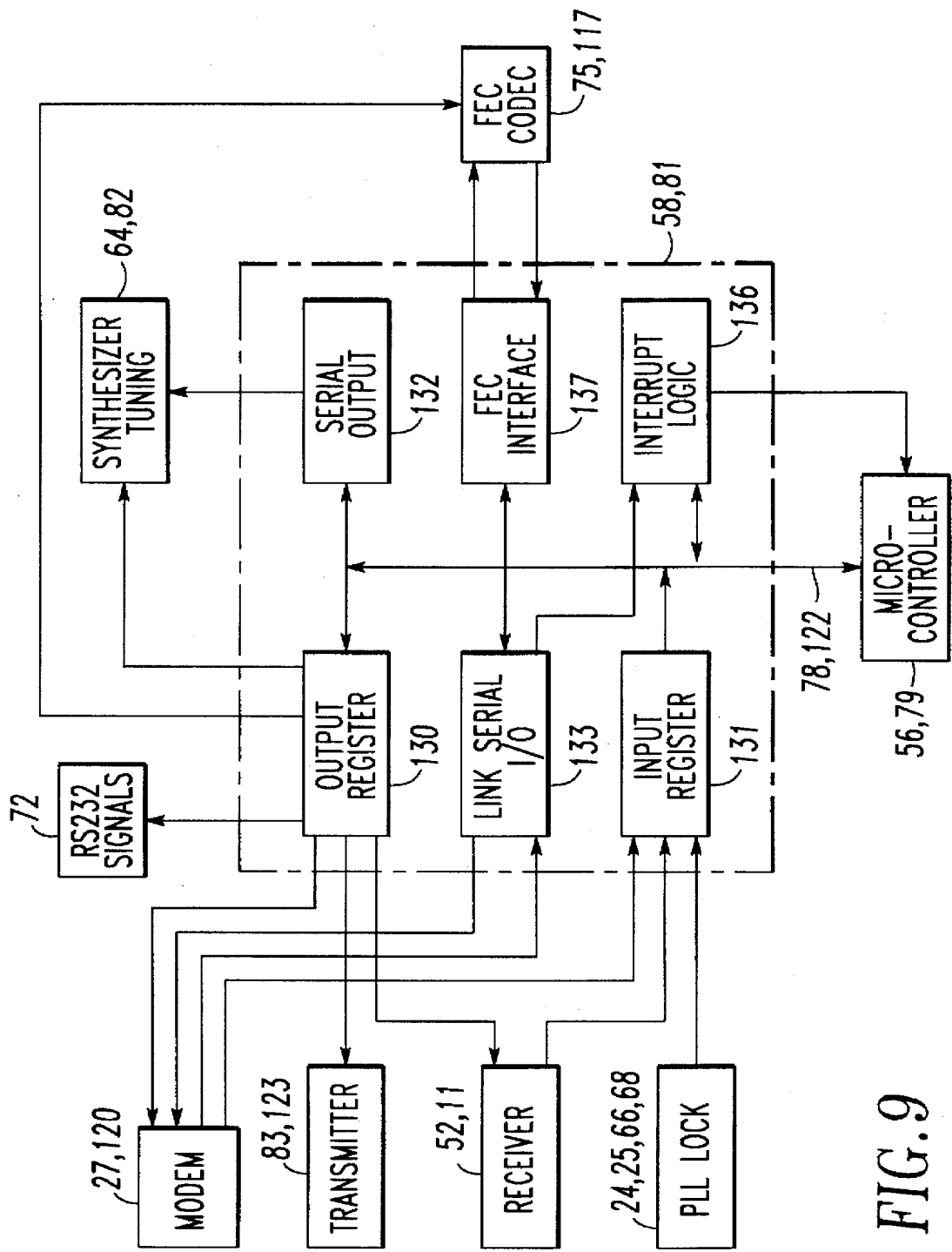
FIG. 9 is a function block diagram of the ASICs within each remote transceiver and base transceiver.

Referring to FIG. 9, the ASICs 58,81 within the respective remote transceiver 18 and base transceiver 22 each contain interfaces for data flow between the RF circuitry, respective microcontrollers 56,79, respective FEC devices 75,117, and I/O registers for modem control, PLL tuning, serial link data and control signals for the RS232 interface 72.

In particular, the microcontrollers 56,79 are coupled with the respective ASICs 58,81 via the respective microcontoller data buses 78,122. The ASICs 58,81 contain output registers 130 coupled with the RS232 interface 72 and respective ones of modems 27,120, transmitters 83,123, receivers 52,112, FEC devices 75,117 and synthesizers 64,82. The ASICs 58,81 include an input port 131 coupled with the respective ones of receivers 52,112, phase lock loops 24,25, 66,68, and digital inputs for signal status of respective modems 27,120. The serial output 132 may be a 21 bit shift register coupled with a respective synthesizer 64,82 for providing frequency control data from the microcontroller 56,79 for frequency hopping. The link serial I/O 133 is coupled with respective modems 27,120 for sending transmit data thereto and receiving reception data therefrom. The interrupt logic 136 is coupled with a respective microcontroller 56,79 for interrupt based on enables for sync detection, inverse sync detection, transmit data empty and receive data ready.

The ASICs 58,81 each additionally include a FEC interface 137 coupled with a respective FEC device 75,117 for matching the timing with a respective microcontroller 56,79. In particular, the FEC interface 137 matches the synchronous operation of the FEC device 75,117 at 4.8 MHz to the asynchronous bus operations of the respective microcontroller 56,79 at 14.7456 MHz. This logic forces all FEC transfers to be timed with respect to the FEC clock using holding registers under control of state machines triggered by the microcontroller 56,79 read or write to the interface.

Figure 10:
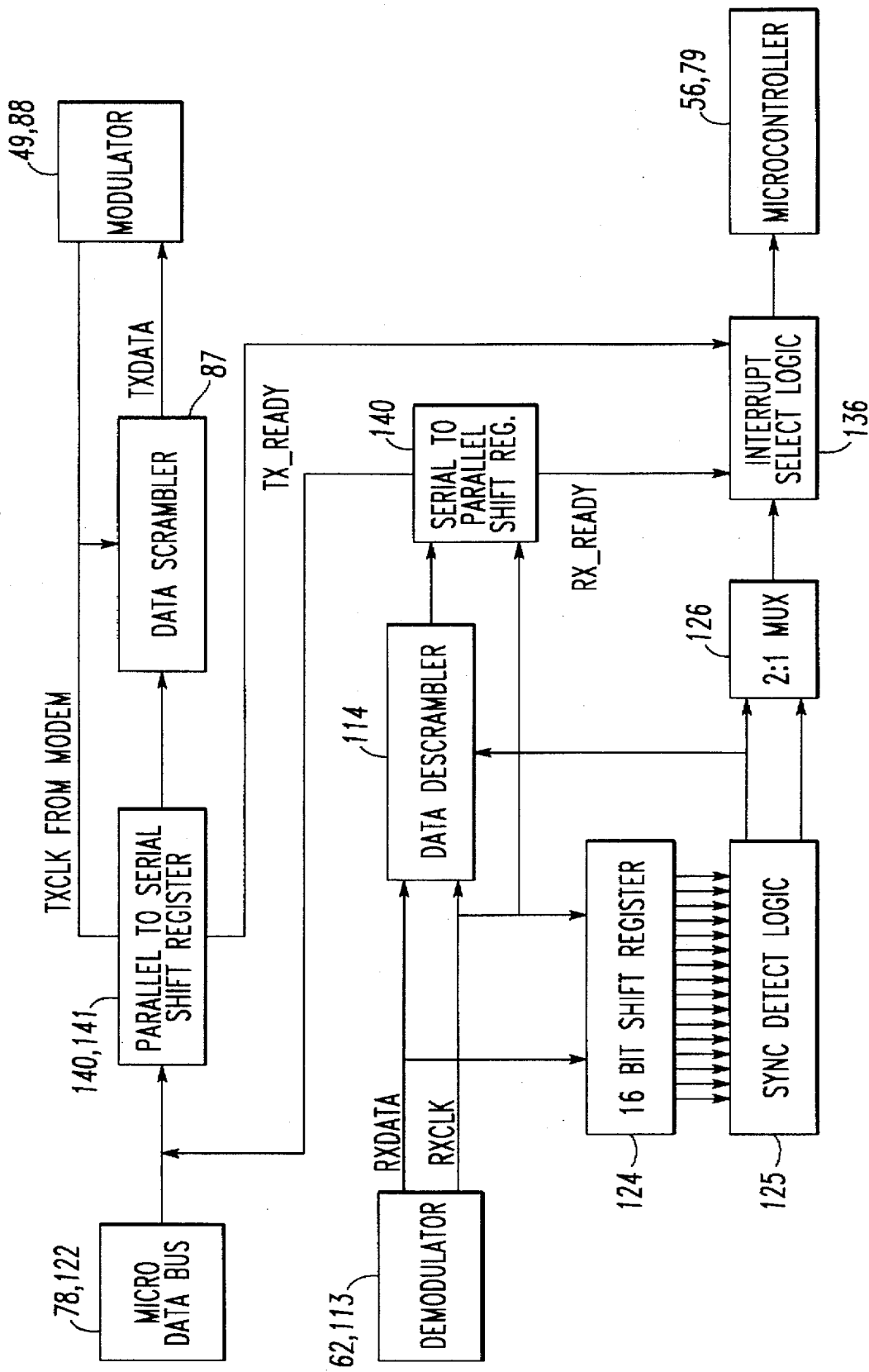
FIG. 10 is a functional block diagram of the data flow within the ASICs.

Data flow within the ASICs 58,81 will be described with reference to FIG. 10. Receiver and transmitter serial digital interfaces or shift registers 140,141 within each ASIC 58,81 provide the conversion between the parallel microcontroller buses 78,122 and the separately clocked serial I\O to the modem circuitry. Each modem 27,120 generates the transmit and receive clocks separately, requiring two sets of synchronous circuitry. A link interrupt may be generated in logic 136 for the microcontroller 56,79 by either the respective transmitter 83,123 being ready for a data write signaled by Tx_Ready or the receiver 52,112 having data to be ready to be read signaled by Rx_Ready, or detection of sync or inverse sync by the detection logic 125.

Each transmitter 83,123 utilizes a parallel to serial shift register with holding register 141 such that the microcontroller 56,79 only needs to monitor a transmit ready flag to periodically load the shift register 141. The shift register 141 output is applied to the data scrambler 87 to avoid long groups of the same bit value being sent to the modem 27,120. The scrambled output is applied to the modulator 49,88 within respective modem 27,120 for conversion to a GMSK modulated linear signal that is applied to the respective synthesizer 64,82 for FM modulation. The startup of the shift register 141 and data scrambler 87 is synchronous to form a known sequence at all times.

The synchronization of the receivers 52,112 occurs based on the received data and establishes the byte\word boundary and the startup of the data descrambler 114 from the initial conditions. The sync pattern may be sent at the start of a data packet to align the receiver 52,112 to within a bit. Sync is captured by a second shift register 124 which in turn drives pattern matching logic 125. Sync may occur when 15 out of 16 bits are matched for low chance of false detection. Inverse sync is also tested to support the search methods where inverse sync is sent at the end of a data packet. Control signals Scramble_On and Sync_Dir are from the ASIC output port 130

The frequency hopping spread spectrum consists of an RF carrier whose center frequency is "hopped" over many frequencies. The base station 10 allocates all frequencies of the hop set and keeps a record of the hop frequencies associated with a transceiver pair which includes a remote transceiver 18 and a corresponding base transceiver 22. The hop set programmed into a remote transceiver 18 is set by the base station 10 to be mutually orthogonal to the hop set of all other transceivers. This ensures that within a single network no transceiver 18,22 is operating on the same frequency as another transceiver 18,22 during the same hop period.

The frequency hopping spread spectrum uses multiple frequencies within a band for RF transmission and reception. Each transceiver 18,22 tracks both the frequency and timing in order to properly receive and decode the transmitted information. Multiple transceivers 18,22 may use the same sequence of frequencies if the relative timing is different such that no two transceivers 18,22 utilize the same frequency at the same time.

The hop frequencies within the 902 MHz–928 MHz band are preferably no less than 50 KHz apart. Therefore, there are over 448 possible frequencies which may be utilized. The hop index should be based on 64 steps and 7 of base stations 10 may be utilized with 64 frequencies for each group. Table 1 shows the frequency allocation among 7 of the base station 10 hop sets.

In order to meet current spread spectrum regulations, the hopping among a set of frequencies is based on a pseudorandom sequence. The sequence is generated either from a lookup table or using an algorithm within the firmware running on microcontroller 56, 79. Given an index into the sequence (e.g., hop number 4 out of 64 total values), the microcontroller will generate the pseudorandom number (e.g., hop number 4 should use the 25th frequency, 5 should use the 55th, hop 6 the 19th, etc.). The pseudorandom number is then used to pick the tuned frequency based on Table 1. In this way, all of the remote units using the same base station frequency set are offset at least 7 frequency channels apart at all times to reduce co-channel interference.

TABLE 1

Frequency Allocation Among Channel Hop Sets

| Frequency Selection | Base Station 1 Frequency | Base Station 2 Frequency | Base Station 3 Frequency | Base Station 4 Frequency | Base Station 5 Frequency | Base Station 6 Frequency | Base Station 7 Frequency |
|---|---|---|---|---|---|---|---|
| 1 | 1 | 2 | 3 | 4 | 5 | 6 | 7 |
| 2 | 8 | 9 | 10 | 11 | 12 | 13 | 14 |
| 3 | 15 | 16 | 17 | 18 | 19 | 20 | 21 |
| ... continued through rest of hops to end of hop sequence ... | | | | | | | |
| 64 | 442 | 443 | 444 | 445 | 446 | 447 | 448 |

The use of a time offset on the frequency hop indexing is preferred since multiple remote transceivers 18 may communicate with a single base station 10. As shown in Table 2, an offset of 2 indexes provides frequency separation such that when a first remote transceiver 18a uses the third random frequency index, the second remote transceiver 18b of the same base station 10 uses the first random frequency index. This time offset occurs over the 64 possible frequencies, where all remote transceivers 18 and base transceivers 22 use the same pseudorandom sequence. The serial party line 37 coordinates all of the base transceivers 22 timing such that they all have the same hop timing.

TABLE 2

Multiple Users on the First Base Station

| Hop Counter | User #1 Index | User #2 Index | User #3 Index | User #4 Index | User #5 Index | User #6 Index | User #32 Index |
|---|---|---|---|---|---|---|---|
| 0 | 1 | 15 | 29 | 43 | 57 | 71 | 435 |
| 1 | 8 | 22 | 36 | 50 | 64 | 78 | 442 |
| 2 | 15 | 29 | 43 | 57 | 71 | 85 | 1 |
| ... continued through rest of hop counter sequencing ... | | | | | | | |
| 63 | 442 | 8 | 22 | 36 | 50 | 64 | 428 |

By offsetting with indexes, timing is relaxed to allow for some time error without the same frequency being used by multiple remote transceivers 18 of the same base station 10.

Data flow between the patient monitor 16 and the base station 10 is mostly from the patient monitor 16 to the base station 10 (e.g., 8:1 ratio allowing for occasional base station 10 commands to the patient monitor 16 for patient alarms and setup). Transmit and receive swapping is such that a remote transceiver 18 transmits data for 8 hops and then receives 1 hop of command data from the base station 10. The transmission from the base station 10 will occur on the same frequency over a group of hops for each respective base station 10 and the next transmission frequency would be 9 indexes away in the hop sequence. The frequency is reused by the remote transceivers 18 during the sequencing.

The operation of the base station 10 RF communications 150 has two modes: synchronization and data flow as shown in FIG. 11a. During synchronization, the base station 10 transmits a data burst every 9 hops while the remote transceiver 18 attempts to search for the correct frequency and timing. By scanning the frequencies (e.g., 64) faster than the hopping of the base station 10, the remote transceiver 18 can eventually capture some of the correct hop transmission. Each data burst has a repetition of sync characters and address information, followed by an inverse sync at the end of the transmission. The remote transceiver 18 will detect the syncs, verify the address, and then measure the time of the inverse sync reception. This serves to time align the remote transceiver 18 with the base station 10 transmit time and frequency hopping, allowing the remote to respond during the 8 hops following the base station 10 transmission. When the sync acknowledgment 149 is sensed by the base station 10, the data flow portion 152 of interaction begins where the remote transceiver 18 begins to transmit sensor data 153 to the base station for 8 hops out of 9. The base station 10 continues to transmit data 154 every 9th hop both for command and as a timing calibration.

FIG. 11b represents the transmission of data from the remote transceivers 18 to the base transceivers 22 during a portion of the data hop sequence 152 once the transceivers are synchronized. In particular, a remote transceiver 18 transmits information for 8 transmit hops 153 and listens for information from the respective base transceiver 22 for a single reception hop 154 and the pattern is repeated during the data hop sequence 152.

During a hop sequence 152, the locked transceivers 18,22 will bounce over a plurality of frequencies at a specified rate. For example, 64 frequencies may be included within a hop sequence 152 and the frequency may change 32 times a second.

FIG. 11c represents the data transmission within a single transmit hop 153. The transmit circuitry is shut off for a specified time period (e.g., 0.1 ms) of power down 155a. The phase lock loops 66,68 are retuned by microcontroller 56,79 to the next hop frequency during a tuning period 156 (e.g. 2 ms). The microcontroller 56,79 powers up the transmit circuitry during a power up period 157 and sends a TRANSMIT ENABLE signal to transmit logic 17. Thus, the microcontroller 56,79 begins to send sync characters 158 to lock in ASIC circuitry 58,81 in the transceivers 18,22 to the actual bit.

Next, a unit address 159 is transmitted identifying the remote transceiver 18 or base transceiver 22 and transmit control logic 160 which specifies that a data frame follows and identifies the hop number within the hop sequence 152. The microcontroller 56,79 next sends a number of data bytes 161 (e.g., 80 bytes) with zero padding followed by a number of FEC check bytes 162 (e.g., 40). The transmitter circuitry is next powered down 155b before the next hop. The receiving transceiver 18,22 may decide to abort data flow and resynchronize if there are enough errors within the unit address 159 and transmit control logic 160.

While preferred embodiments of the invention have been shown and described herein, it will be appreciated by those skilled in the art that various modifications and alternatives to the disclosed embodiments may be developed in light of the overall teachings of the disclosure. Accordingly, the disclosed embodiments are meant to be illustrative only and not limiting to the scope of the invention which is to be given the full breadth of the following claims and all equivalents thereof.

We claim:

1. A communication system for conveying biomedical data between a plurality of patient monitors and a centralized base station, comprising:

a transmit antenna;

a receive antenna separated from said transmit antenna;

a plurality of base transceivers within said base station;

means including a single transmit port coupling said base transceivers of said plurality to said transmit antenna;

means including a single receive port coupling said base transceivers of said plurality to said receive antenna;

a plurality of remote transceivers each coupled with one of said patient monitors and corresponding to a respective one of said base transceivers for communicating biomedical data therewith;

said base transceivers and said remote transceivers each having at least one tuning device for varying the center frequency thereof and a microcontroller coupled with each of said at least one tuning device for controlling the varying of the center frequency according to a hop sequence.

2. The communication system of claim 1 wherein said hop sequence of each of said remote transceivers corresponds to said hop sequence of said respective one of said base transceivers.

3. The communication system of claim 1 wherein said hop sequence of each of said base transceivers is orthogonal to said hop sequence of other said base transceivers.

4. The communication system of claim 1 wherein each frequency in said hop sequence is separated from other frequencies therein by at least about 50 kHz.

5. The communication system of claim 1 wherein each said base transceiver and each said remote transceiver is coupled with a forward error correction device for reducing errors within said biomedical data.

6. The communication system of claim 1 wherein each said base transceiver and each said remote transceiver is coupled with a scrambler for one of scrambling and descrambling said biomedical data.

7. The communication system of claim 6 wherein said scrambling removes bit redundancy within said biomedical data.

8. The communication system of claim 1 wherein each said base transceiver and each said remote transceiver is coupled with a modem for one of modulating and demodulating said biomedical data.

9. The communication system of claim 8 wherein said modem provides GMSK modulation and GMSK demodulation of said biomedical data.

10. The communication system of claim 1 wherein said tuning devices are phase lock loops.

11. The communication system of claim 1 further comprising a bus for interconnecting each of said base transceivers and said base station.

12. A communication system for conveying biomedical data between a plurality of patient monitors and a centralized base station, comprising:

a transmit antenna;

a receive antenna separated from said transmit antenna;

a plurality of base transceivers within said base station;

means including a single transmit port coupling said base transceivers of said plurality to said transmit antenna;

means including a single receive port coupling said base transceivers of said plurality to said receive antenna;

a plurality of remote transceivers each coupled with one of said patient monitors and corresponding to a respective one of said base transceivers for communicating biomedical data therewith;

said base transceivers and said remote transceivers each having at least one tuning device for varying the center frequency thereof and a microcontroller coupled with each of said at least one tuning device for controlling the varying of the center frequency according to a hop sequence;

said hop sequence of each of said remote transceivers corresponds to said hop sequence of said respective one of said base transceivers and said hop sequence of each of said base transceivers is orthogonal to said hop sequence of other said base transceivers.

13. The communication system of claim 12 wherein each frequency in said hop sequence is separated from other frequencies therein by at least about 50 kHz.

14. The communication system of claim 13 wherein each said base transceiver and each said remote transceiver is coupled with a forward error correction device for reducing errors within said biomedical data.

15. The communication system of claim 14 wherein each said base transceiver and each said remote transceiver is coupled with a scrambler for one of scrambling and descrambling said biomedical data.

16. The communication system of claim 15 wherein said scrambling removes bit redundancy within said biomedical data.

17. The communication system of claim 16 wherein each said base transceiver and each said remote transceiver is coupled with a modem for one of modulating and demodulating said biomedical data.

18. The communication system of claim 17 wherein said modem provides GMSK modulation and GMSK demodulation of said biomedical data.

19. The communication system of claim 18 wherein said tuning devices are phase lock loops.

20. The communication system of claim 19 further comprising a bus for interconnecting each of said base transceivers and said base station.

* * * * *